(12) United States Patent
Yamasaki et al.

(10) Patent No.: US 11,162,930 B2
(45) Date of Patent: Nov. 2, 2021

(54) INSPECTION APPARATUS AND INSPECTION SYSTEM

(71) Applicant: KYOCERA Corporation, Kyoto (JP)

(72) Inventors: Hirohide Yamasaki, Yokohama (JP); Shinichi Kobori, Saitama (JP)

(73) Assignee: KYOCERA Corporation, Kyoto (JP)

( * ) Notice: Subject to any disclaimer, the term of this patent is extended or adjusted under 35 U.S.C. 154(b) by 189 days.

(21) Appl. No.: 16/079,447

(22) PCT Filed: Feb. 17, 2017

(86) PCT No.: PCT/JP2017/005897
§ 371 (c)(1),
(2) Date: Aug. 23, 2018

(87) PCT Pub. No.: WO2017/145933
PCT Pub. Date: Aug. 31, 2017

(65) Prior Publication Data
US 2019/0056370 A1   Feb. 21, 2019

(30) Foreign Application Priority Data
Feb. 26, 2016   (JP) .............................. JP2016-035217

(51) Int. Cl.
*G01N 33/02*   (2006.01)
*A23L 5/00*   (2016.01)
*G01N 29/02*   (2006.01)

(52) U.S. Cl.
CPC ................ *G01N 33/02* (2013.01); *A23L 5/00* (2016.08); *G01N 29/022* (2013.01)

(58) Field of Classification Search
None
See application file for complete search history.

(56) References Cited

U.S. PATENT DOCUMENTS

| | | | | |
|---|---|---|---|---|
| 2011/0054801 A1* | 3/2011 | Hilborne | ................ | G01N 33/14 702/22 |
| 2014/0116158 A1* | 5/2014 | Minteer | .................. | B01L 3/502 73/863.01 |
| 2014/0137587 A1* | 5/2014 | Hitzelberger | ......... | F25D 17/042 62/228.1 |

(Continued)

FOREIGN PATENT DOCUMENTS

| | | | |
|---|---|---|---|
| CN | 102142058 A | * | 8/2011 |
| JP | 2001-183323 A | | 7/2001 |

(Continued)

OTHER PUBLICATIONS

English Translation of JP 2001/183323 (Year: 2020).*

*Primary Examiner* — Matthew D Krcha
(74) *Attorney, Agent, or Firm* — Studebaker & Brackett PC (57) ABSTRACT

An inspection apparatus includes a container, first and second detectors, and a controller. The container stores a specimen. The first detector detects a substance emitted by the specimen stored in the container. The second detector detects a different component than the substance in the atmosphere inside the container. The controller corrects the result of detection of the substance by the first detector on the basis of the component detected by the second detector and judges a quality of the specimen.

14 Claims, 4 Drawing Sheets

(56) References Cited

U.S. PATENT DOCUMENTS

2014/0300891 A1* 10/2014 Alfano ............... G01N 21/6486
                                                              356/51
2017/0160005 A1*  6/2017 Park .................... F25D 29/005
2017/0263100 A1*  9/2017 Johnston ............. F25D 29/008

FOREIGN PATENT DOCUMENTS

JP         2001183323 A  *  7/2001
JP         2005-173675 A     6/2005

* cited by examiner

INSPECTION APPARATUS AND INSPECTION SYSTEM

CROSS-REFERENCE TO RELATED APPLICATION

The present application claims priority to and the benefit of Japanese Patent Application No. 2016-035217 filed Feb. 26, 2016, the entire contents of which are incorporated herein by reference.

TECHNICAL FIELD

The present disclosure relates to an inspection apparatus and an inspection system.

BACKGROUND

A food product management system for managing the deterioration status of a food product is known. For example, a food product management system collects information related to the deterioration status of a food product stored in a container and manages the deterioration status.

SUMMARY

An inspection apparatus according to an embodiment includes a container, a first detector, a second detector, and a controller. The container stores a specimen. The first detector detects a substance emitted by the specimen stored in the container. The second detector detects a different component than the substance in the atmosphere inside the container. The controller corrects the result of detection of the substance by the first detector on the basis of the component detected by the second detector and judges a quality of the specimen.

An inspection system according to an embodiment includes a detection apparatus and an inspection apparatus. The detection apparatus includes a container that stores a specimen, a first detector that detects a substance emitted by the specimen stored in the container, a second detector that detects a different component than the substance in an atmosphere inside the container, and a communication interface that transmits information related to the substance detected by the first detector and information related to the component detected by the second detector to the inspection apparatus. The inspection apparatus includes a communication interface that receives the information related to the substance and the information related to the component from the detection apparatus and a controller that, on the basis of the received information related to the substance and the received information related to the component, corrects a result of detection of the substance by the detection apparatus on the basis of the component and judges a quality of the specimen.

DETAILED DESCRIPTION

In case that a food product management system continuously monitors the deterioration status of the food product stored in the container, even if the user of the food product management system wishes to learn the deterioration status of a food product not stored in the container, for example, he cannot do so immediately. The present disclosure can improve the usefulness of an inspection apparatus and an inspection system.

Embodiments are described below in detail with reference to the drawings.

First Embodiment

Figure 1:
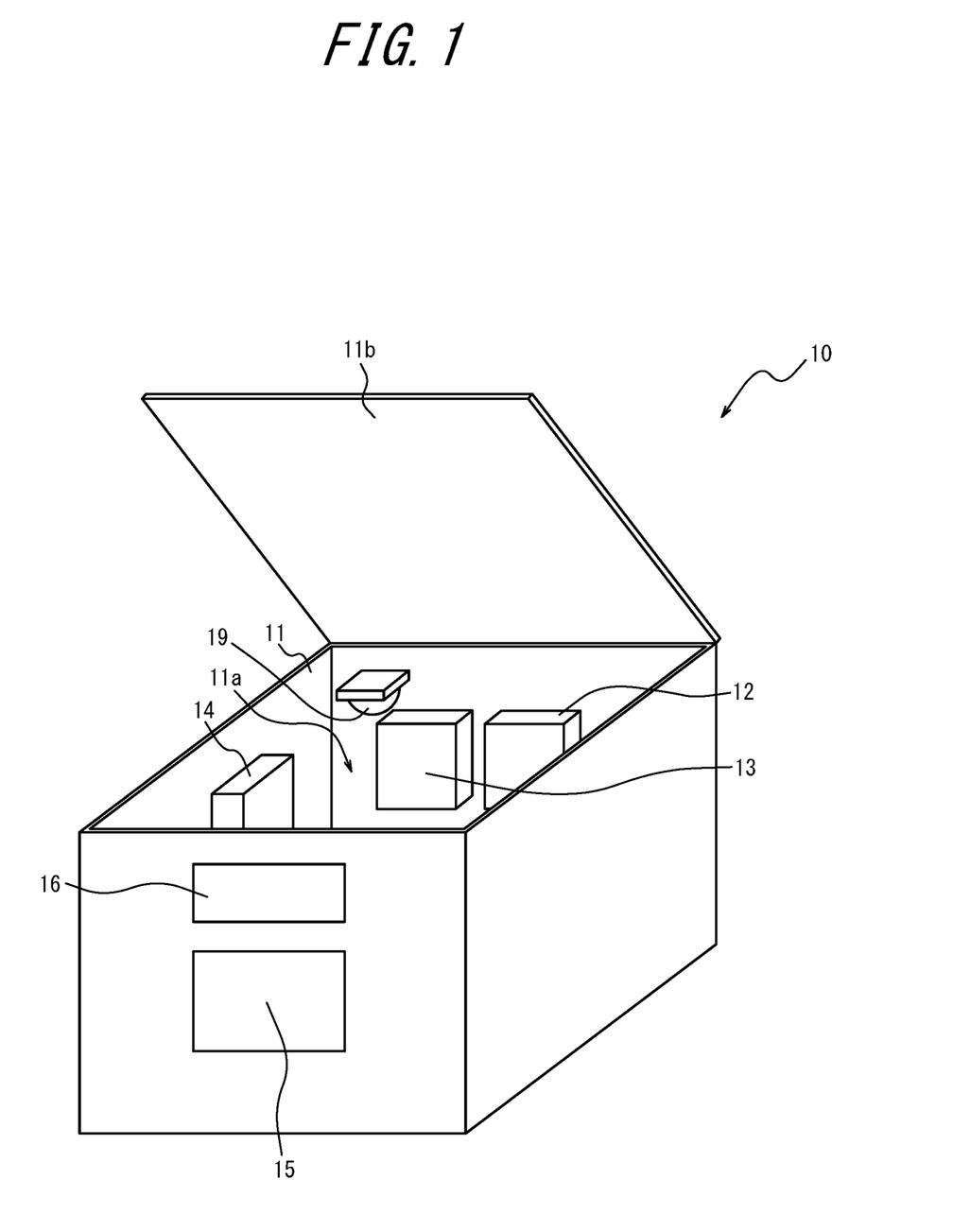
FIG. 1 is an external perspective view schematically illustrating an inspection apparatus according to a first embodiment.

FIG. 1 is an external perspective view schematically illustrating an inspection apparatus according to a first embodiment. An inspection apparatus 10 includes a container 11, a first detector 12, a second detector 13, a deodorizer 14, a notification interface 15, an input interface 16, a controller 17, a memory 18, and a camera 19. Details of the controller 17 and the memory 18 are provided below with reference to the functional block diagram in FIG. 2.

The inspection apparatus 10 executes an inspection process in accordance with a predetermined inspection operation while a specimen is stored in the container 11. In other words, when the inspection apparatus 10 is to execute the inspection process, the user stores the specimen inside the container 11. While the specimen is stored in the container 11, the inspection apparatus 10 uses the first detector 12 to detect a substance emitted by the specimen. Along with detecting a substance using the first detector 12, the inspection apparatus 10 detects a predetermined component inside the container 11 using the second detector 13. The predetermined component detected by the second detector 13 differs from the substance emitted by the specimen and detected by the first detector 12. In particular, the predetermined component detected by the second detector 13 is a component that can reduce the detection accuracy of the substance by the first detector 12. The inspection apparatus 10 judges a quality of the specimen after correcting the result of detection of the substance by the first detector 12 on the basis of the predetermined component detected by the second detector 13. The inspection apparatus 10 executes the inspection process in this way in accordance with the inspection operation. The notification interface 15 provides notification of the result of the inspection process. An example of the specimen being a food product is described below in the present embodiment.

The container 11 is, for example, sealable. The specimen is removably stored in a containment chamber (inspection chamber) 11a of the container 11. The container 11 includes a pivotable lid 11b. The user of the inspection apparatus 10 opens the lid 11b and stores a food product in the containment chamber 11a. The lid 11b need not be pivotable. It suffices for the lid 11b to be capable of sealing the containment chamber 11a. For example, the container 11 may include a lid 11b that is slidable upward or sideways. The container 11 for example includes a tray, on the bottom of the containment chamber 11a, on which the food product can be placed.

The first detector 12 detects a substance emitted by the food product that is the specimen. The first detector 12 may, for example, be an odor sensor that detects an odor emitted by the food product. The first detector 12 may, for example, be a gas sensor that detects a gas emitted by the food product. Specifically, the first detector 12 includes a sensitive membrane and a transducer. The sensitive membrane adsorbs gas molecules that are the source of the odor, and the transducer converts detection of the gas molecules in the sensitive membrane into an electric signal.

The first detector 12 may, for example, be provided with a quartz crystal resonator type odor sensor that includes a sensitive membrane, made of an organic thin film, and a quartz crystal resonator. The quartz crystal resonator type odor sensor detects an odor by a change in the resonance frequency of the quartz crystal resonator when gas molecules are adsorbed on the sensitive membrane. The quartz crystal resonator functions as a transducer that converts detection of gas molecules into an electric signal.

The first detector 12 may, for example, be provided with a semiconductor gas sensor. The semiconductor gas sensor detects the gas concentration by a change in the resistance of a metal oxide semiconductor when gas molecules are adsorbed on the metal oxide semiconductor. The oxide semiconductor functions as a transducer that converts detection of gas molecules into an electric signal. The first detector 12 may, for example, be provided with an infrared absorption spectrum type gas sensor, an electrochemical gas sensor, a contact combustion type gas sensor, a biosensor, or the like.

To adsorb different types of gas molecules, for example, the first detector 12 may be provided with a plurality of types of sensitive membranes or metal oxides. The first detector 12 may be provided with a plurality of quartz crystal resonator type odor sensors, a plurality of semiconductor gas sensors, or a combination of these sensors. The first detector 12 transmits the electric signal converted by the transducer to the below-described controller as odor-related information. The first detector 12 is, for example, located inside the container 11. In FIG. 1, the first detector 12 is located on an inner side wall of the container 11.

The second detector 13 detects a predetermined component, in the atmosphere inside the container 11, that differs from the substance detected by the first detector 12. As an example, the second detector 13 in the present embodiment detects moisture inside the container 11. The second detector 13 is, for example, a humidity sensor. Specifically, the second detector 13 may be an electric hygrometer that measures humidity using a sensor constituted by a semiconductor or the like. The second detector 13 may be another type of hygrometer, such as a tension hygrometer, a wet/dry hygrometer, or a dew point hygrometer. The second detector 13 may, for example, be a quartz crystal resonator provided with a sensitive membrane that adsorbs water molecules. The second detector 13 may, for example, be a metal oxide semiconductor provided with a sensitive membrane that adsorbs water molecules. In FIG. 1, the second detector 13 is located on an inner side wall of the container 11.

The deodorizer 14 performs a deodorization process on the inside of the container 11. For example, the deodorizer 14 is configured by a degassing apparatus, a deodorizing apparatus, or the like. When the deodorizer 14 is configured to include a degassing apparatus, the deodorizer 14 deodorizes the container 11 by expelling (degassing) gas molecules from inside the container 11 to the outside. When the deodorizer 14 is configured to include an ozone deodorizing apparatus, the deodorizer 14 discharges ozone into the container 11. The discharged ozone decomposes gas molecules to deodorize the inside of the container 11. When the deodorizer 14 is configured to include an oxygen cluster deodorizing apparatus, the deodorizer 14 ionizes the oxygen molecules inside the container 11. The ionized oxygen molecules (oxygen cluster ions) subject gas molecules inside the container 11 to ion decomposition to deodorize the inside of the container 11.

The deodorizer 14 is, for example, located inside the container 11. In FIG. 1, the deodorizer 14 is located on an inner side wall of the container 11.

The notification interface 15 provides notification of the result of the inspection process by the inspection apparatus 10. The notification interface 15 can, for example, provide notification by a visual method using image, character, or color display, light emission, or the like; an auditory method using audio or the like; or a combination of these methods. To provide notification with a visual method, the notification interface 15 may be a display device that provides notification by displaying images or characters. The notification interface 15 may, for example, provide notification by emitting light with an LED or the like. To provide notification with an auditory method, the notification interface 15 may be a speaker or other such sound generating device that provides notification by outputting an alarm, audio guidance, or the like. The notification interface 15 is not limited to providing notification by a visual or auditory method. Any method recognizable by the subject may be adopted. For example, the notification interface 15 may provide notification with a vibration pattern or the like.

In the example in FIG. 1, the notification interface 15 is a display device located outside of the container 11 and provides notification of the result of the inspection process with images, characters, color, or the like.

The input interface 16 accepts operation input from the user and may be configured by operation buttons (operation keys), for example. The input interface 16 may, for example, be a touchscreen. An input region that accepts operation input from the user may be displayed on a portion of the display device that is the notification interface 15, and the input interface 16 may accept touch operation input by the user to this input region. The user may, for example, instruct the inspection apparatus 10 to start inspection by operating the input interface 16 (by an inspection operation). The user may, for example, input the type of food product that is the specimen by operating the input interface 16.

On the basis of control by the inspection apparatus 10, the camera 19 captures an image of the specimen. Information related to the imaged specimen is transmitted to the below-described controller along with the odor-related information.

Figure 2:
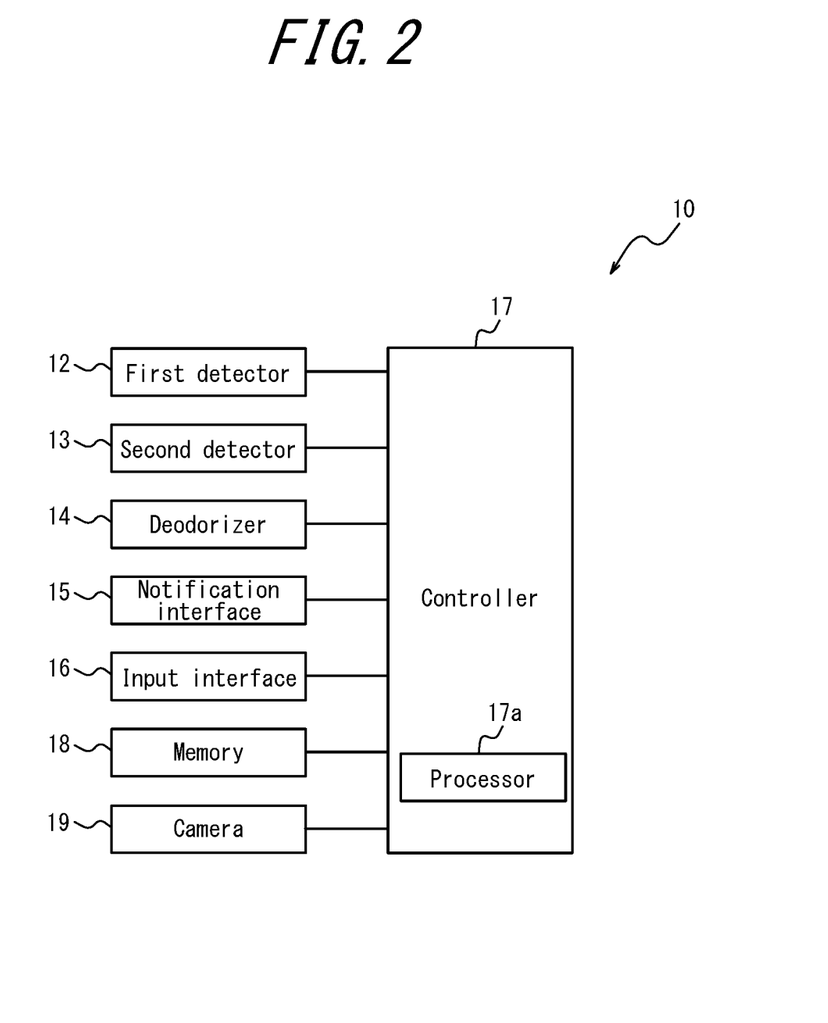
FIG. 2 is a functional block diagram illustrating the schematic configuration of the inspection apparatus in FIG. 1.

FIG. 2 is a functional block diagram illustrating the schematic configuration of the inspection apparatus 10 in FIG. 1. As illustrated in FIG. 2, the inspection apparatus 10 includes the first detector 12, the second detector 13, the deodorizer 14, the notification interface 15, the input interface 16, the controller 17, the memory 18, and the camera 19.

The controller 17 is a processor that controls and manages the inspection apparatus 10 overall, starting with the functional blocks of the inspection apparatus 10. The controller 17 is a processor, such as a central processing unit (CPU), that executes a program prescribing control procedures. Such a program is, for example, stored in the memory 18 or on an external storage medium.

To provide control and processing capability for executing various functions, as described below in greater detail, the inspection apparatus 10 is provided with the controller 17, which includes one or more processors 17a.

In various embodiments, the one or more processors 17a may be implemented as a single integrated circuit or as a plurality of communicatively connected integrated circuits and/or discrete circuits. The one or more processors 17a can be implemented with a variety of known techniques.

In an embodiment, the processor 17a includes one or more circuits or units configured to execute one or more data calculation procedures or processes by executing instructions stored in related memory, for example. In another embodiment, the processor 17a may be firmware (such as discrete logic components) configured to execute one or more data calculation procedures or processes.

In various embodiments, the processor 17a may include one or more processors, controllers, microprocessors, microcontrollers, application specific integrated circuits (ASIC), digital signal processors, programmable logic devices, field programmable gate arrays, any combination of these devices or structures, or a combination of other known devices and structures, to execute the below-described functions.

The controller 17 executes the inspection process using the inspection apparatus 10 by controlling the entire inspection apparatus 10. For example, the controller 17 activates the first detector 12 on the basis of predetermined operation input that the user of the inspection apparatus 10 provides to the input interface 16. The first detector 12 activated by the controller 17 starts to detect an odor emitted by the food product. The controller 17 acquires information related to the odor detected by the first detector 12 from the first detector 12.

The controller 17 activates the second detector 13. The controller 17 activates the second detector 13 at an appropriate time on the basis of the component to be detected by the second detector 13, the detection method, and the like. For example, the controller 17 may activate the second detector 13 on the basis of predetermined operation input that the user provides to the input interface 16. The controller 17 may, for example, activate the first detector 12 and the second detector 13 simultaneously. The controller 17 may, for example, activate the second detector 13 a predetermined length of time before activating the first detector 12 or a predetermined length of time after activating the first detector 12. The controller 17 may continuously keep the second detector 13 activated. In the present embodiment, the controller 17 is described as continuously keeping the second detector 13 activated.

In the present embodiment, the second detector 13 continuously detects moisture (humidity) inside the container 11. The controller 17 acquires information related to the moisture detected by the second detector 13 from the second detector 13. The controller 17 may, for example, acquire the moisture-related information continuously or only at the time of odor detection by the first detector 12. The moisture-related information may, for example, be the humidity detected by a humidity sensor. The moisture-related information may, for example, be a signal output by the second detector 13, which detects water molecules.

The controller 17 corrects the result of odor detection by the first detector 12 on the basis of information related to the moisture, detected by the second detector 13, in the container 11. The controller 17 may, for example, calculate a correction coefficient on the basis of the humidity detected by the second detector 13. The controller 17 may, for example, calculate a correction coefficient on the basis of the output signal from the second detector 13. The controller 17 may correct the odor-related information acquired from the first detector 12 on the basis of the calculated correction coefficient. The controller 17 may, for example, subtract the output signal of the second detector 13 from the output signal of the first detector 12 to correct the odor-related information acquired from the first detector 12. As a result, the controller 17 can correct the amount of moisture included in the component for odor detection detected by the first detector 12.

The controller 17 judges the quality of the food product on the basis of the corrected odor detection result. For example, the first detector 12 may include a plurality of different odor sensors that adsorb ethylene, ammonia, alcohol, aldehyde, and sulfur gas molecules. The controller 17 may correct a plurality of signals detected by the plurality of odor sensors and judge the quality of the food product on the basis of the corrected plurality of signals. The components of gas molecules that are the source of the odor emitted by a food product, the ratio of the components, and the like differ depending on the food product and the quality of the food product. Therefore, the controller 17 judges the quality of a food product on the basis of odor-related information, i.e. the components of gas molecules that are the source of the odor, the ratio of the components, and the like. The controller 17 may, for example, judge the quality of the food product on the basis of the corrected outputs of a plurality of odor sensors and the ratio of the outputs. The controller 17 may, for example, judge the quality of the food product on the basis of features (output value, time constant, or the like) of the corrected response of a plurality of odor sensors. The first detector 12 may, for example, include a plurality of ethylene, alcohol, sulfur, and ammonia type odor sensors. When judging the quality of a vegetable, for example, the controller 17 may judge that the quality has deteriorated when the outputs of the alcohol, sulfur, and ammonia type odor sensors among the corrected plurality of odor sensor outputs increase to a predetermined value or higher.

To judge the quality of a food product, the controller 17 refers to information (data), stored in the memory 18, associating the odor emitted by a food product and the quality of the food product. Here, the quality of a food product refers to the properties or qualities of the food product.

The quality of the food product may, for example, refer to whether the food product is spoiled. In this case, the controller 17 judges whether the food product is spoiled on the basis of the odor-related information. The controller 17 may judge the degree of spoiling of the food product.

The quality of the food product may, for example, refer to whether the food product is ripe. In this case, the controller 17 judges whether the food product is ripe on the basis of the odor-related information. The controller 17 may judge when the food product will be ripe.

The quality of the food product may, for example, refer to the degree of aging of the food product. In this case, the controller 17 judges the degree of aging of a food product, i.e. the degree to which the food product (such as meat) has aged, on the basis of the odor-related information.

The quality of the food product may, for example, refer to the freshness of the food product. In this case, the controller 17 judges the freshness of a food product, i.e. how fresh the food product is, on the basis of the odor-related information.

The quality of the food product may, for example, refer to the production area of the food product. In this case, the controller 17 judges the production area of the food product on the basis of the odor-related information. Specifically, the controller 17 judges whether the food product is domestic or foreign, for example. The controller 17 may judge the specific production area of the food product.

The quality of the food product may, for example, refer to the extent of residual pesticide in the food product. In this case, the controller 17 judges the extent of residual pesticide in the food product, i.e. the amount of residual pesticides in the food product, on the basis of the odor-related information.

The quality of the food product is not limited to the above-described examples and may be any other property or quality related to the food product. The controller 17 may judge the odor using a statistical method, such as principal component analysis, or using a neural network. The controller 17 may generate data by performing a learning process in advance to extract the features of the response of a plurality of odor sensors for each quality of a food product. The controller 17 may store the data after learning in the memory 18. The controller 17 may then judge the quality of the food product on the basis of the degree of matching between the data after learning stored in the memory 18 and the data that is detected by the first detector 12 and corrected. Based on newly detected data, the controller 17 may update the data after learning stored in the memory 18.

The controller 17 may judge the quality of the food product on the basis of the corrected odor detection result and information related to the specimen imaged by the camera 19. The controller 17 may, for example, infer the type of food product on the basis of the information related to the specimen imaged by the camera 19. A plurality of sets of information (data) associating the odor emitted by a food product and the quality of the food product are stored in the memory 18 for each type of food product. The controller 17 may refer to the information (data) corresponding to the inferred type of food product to judge the quality of the food product.

The controller 17 may judge the quality of the food product on the basis of the odor-related information and the food product type input by operation of the input interface 16. In this case, the controller 17 may refer to the information (data) corresponding to the input type of food product to judge the quality of the food product.

The controller 17 provides notification of information related to the judged quality of the food product through the notification interface 15 as the result of the inspection process. As described above, the notification method may be any method recognizable by the subject. When the notification interface 15 is a display device, as illustrated in FIG. 1, the controller 17 provides notification by display of images, characters, or colors on the display device.

The controller 17 may store information related to the judged quality of the food product in the memory 18 as history data, for example.

Before or after the first detector 12 detects an odor, the controller 17 may execute a refresh process to refresh the inside of the container 11. The refresh process is a process to reduce factors that can cause detection errors during odor detection by the first detector 12. The controller 17 may, for example, execute the refresh process by activating the deodorizer 14 to degas or deodorize the inside of the container 11. The controller 17 may, for example, execute the refresh process by resetting the first detector 12. By being reset, the first detector 12 can use the internal state of the container 11 at the time of resetting as a reference to detect a change in the odor inside the container 11 due to an odor emitted by a food product newly stored in the container 11, for example. The controller 17 may reset the second detector 13 as the refresh process when, due to the principle of component detection by the second detector 13, resetting allows a reduction in detection errors of the predetermined component.

The controller 17 can improve the accuracy of odor detection by executing the refresh process before odor detection. The controller 17 can improve the accuracy of odor detection during the next detection process by executing the refresh process after odor detection.

The memory 18 may be configured with a semiconductor memory, a magnetic memory, or the like. The memory 18 stores a variety of information, programs for causing the inspection apparatus 10 to operate, and the like and also functions as a working memory. For example, the memory 18 stores information (data) associating the odor emitted by a food product and the quality of the food product. The memory 18 may, for example, store the result of the detection process by the inspection apparatus 10 as history data.

The camera 19 captures an image of the food product stored in the container 11. The camera 19 transmits information related to the imaged food product to the controller 17. The inspection apparatus 10 may further include an optical emitter to produce a flash when the camera 19 captures an image.

Figure 3:
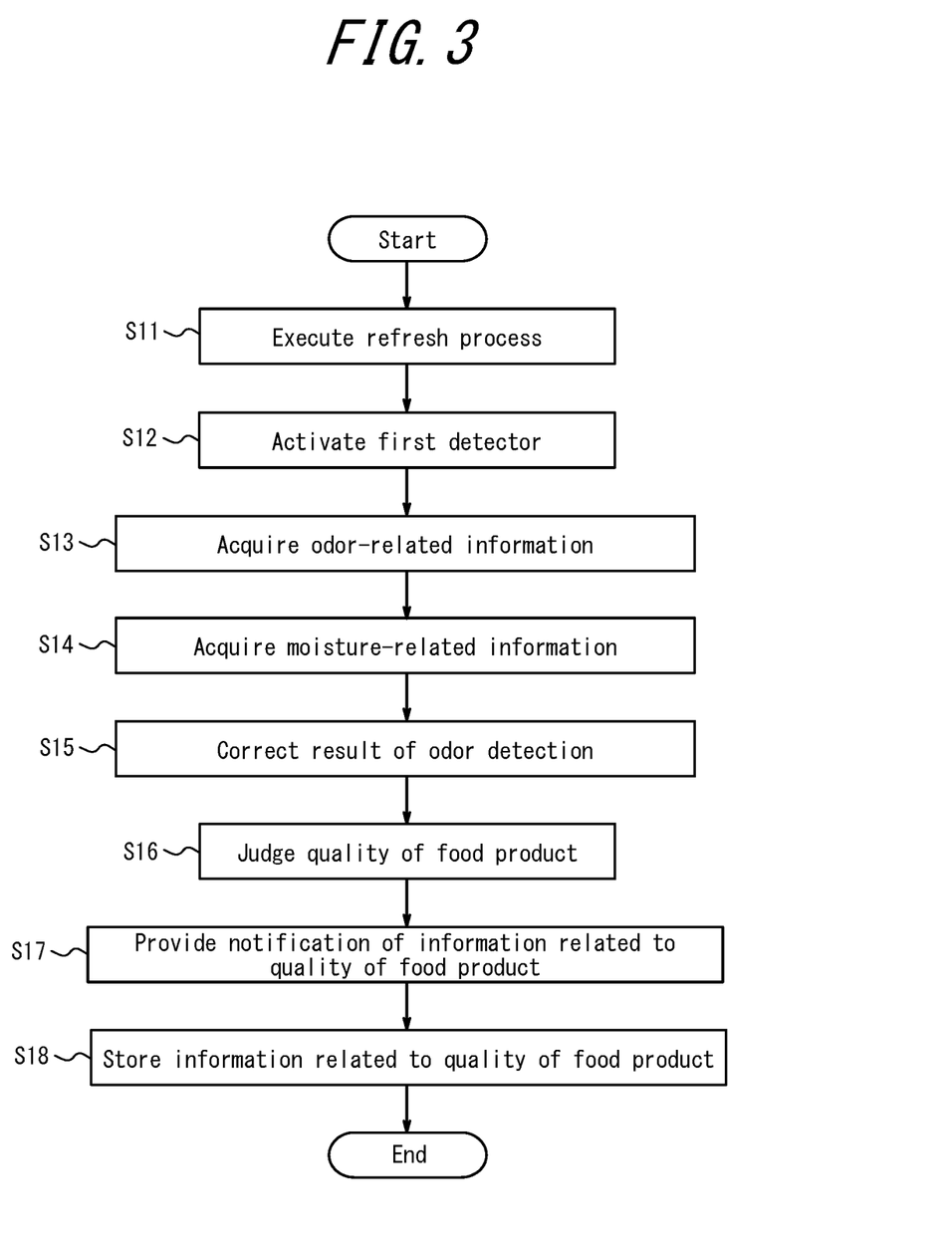
FIG. 3 is a flowchart illustrating an example of an inspection process executed by the controller in FIG. 2.

Next, with reference to the flowchart in FIG. 3, an example of the process executed by the controller 17 when the inspection apparatus 10 executes the inspection process is described. Here, the controller 17 is described as executing the refresh process before the odor detection process by the first detector 12.

To inspect the quality of a food product using the inspection apparatus 10, the user first opens the lid 11b of the inspection apparatus 10 and places the food product to be inspected in the container 11. The user then closes the lid 11b to seal the container 11. Subsequently, the user instructs the inspection apparatus 10 to start the inspection process by operating the input interface 16 (by an inspection operation).

Once the user provides the predetermined operation input, the controller 17 starts the process in FIG. 3.

First, the controller 17 executes the refresh process by, for example, activating the deodorizer 14 (step S11).

Subsequently, the controller 17 activates the first detector 12 (step S12). By being activated by the controller 17, the first detector 12 starts to detect an odor emitted by the food product stored in the container 11.

From the first detector 12, the controller 17 acquires the odor-related information obtained by the first detector 12 (step S13).

From the second detector 13, the controller 17 acquires the information, obtained by the second detector 13, related to the moisture in the atmosphere inside the container 11 (step S14).

On the basis of the acquired moisture-related information, the controller 17 corrects the result of odor detection by the first detector 12 (step S15).

On the basis of the result corrected in step S15, the controller 17 refers to the data stored in the memory 18 to judge the quality of the food product (step S16).

The controller 17 provides notification of information related to the quality of the food product judged in step S16 through the notification interface 15 (step S17). The user can learn the quality of the food product by the notification from the notification interface 15.

The controller 17 stores the information related to the quality of the food product judged in step S16 in the memory 18 (step S18).

Before judging the quality of the food product in step S16, the controller 17 may capture an image of the specimen using the camera 19 and infer the type of food product on the basis of information related to the imaged specimen. In this case, the controller 17 may refer to information (data) corresponding to the inferred type of food product to judge the quality of the food product.

In accordance with an inspection operation, the inspection apparatus 10 according to the present embodiment thus uses the first detector 12 to detect an odor emitted by a food product stored in the container 11. On the basis of the detected odor, the inspection apparatus 10 judges the quality of the food product. Therefore, when the user wishes to learn the quality of a food product, the user can do so immediately by placing the food product in the container 11 and causing the inspection apparatus 10 to execute the inspection process. Accordingly, the inspection apparatus 10 allows the quality of a food product to be inspected in accordance with user need, thereby improving usefulness as compared to known apparatuses.

The inspection apparatus 10 judges a quality of the specimen after correcting the result of detection of the substance by the first detector 12 on the basis of the moisture detected by the second detector 13. When, due to the principle of substance detection, the odor sensor that is the first detector 12 detects moisture along with the substance to be detected, for example, the judgement accuracy of the inspection apparatus 10 therefore improves as compared to when the quality of the specimen is judged only on the basis of the result of detection by the first detector 12.

The inspection apparatus 10 according to the present embodiment allows one inspection apparatus 10 to inspect the quality of a plurality of food products by switching of the food product stored in the container 11.

The inspection apparatus 10 according to the first embodiment has been described as including the first detector 12 that detects an odor, the second detector 13 that detects moisture, and the controller 17 that judges the quality of a food product. The functional units (detectors) that detect an odor and moisture and the functional unit that judges the quality, however, may be provided in separate apparatuses capable of communicating with each other. The case of the functional units that detect an odor and moisture and the functional unit that judges the quality being provided in separate apparatuses is described as a second embodiment with reference to FIG. 4.

Second Embodiment

Figure 4:
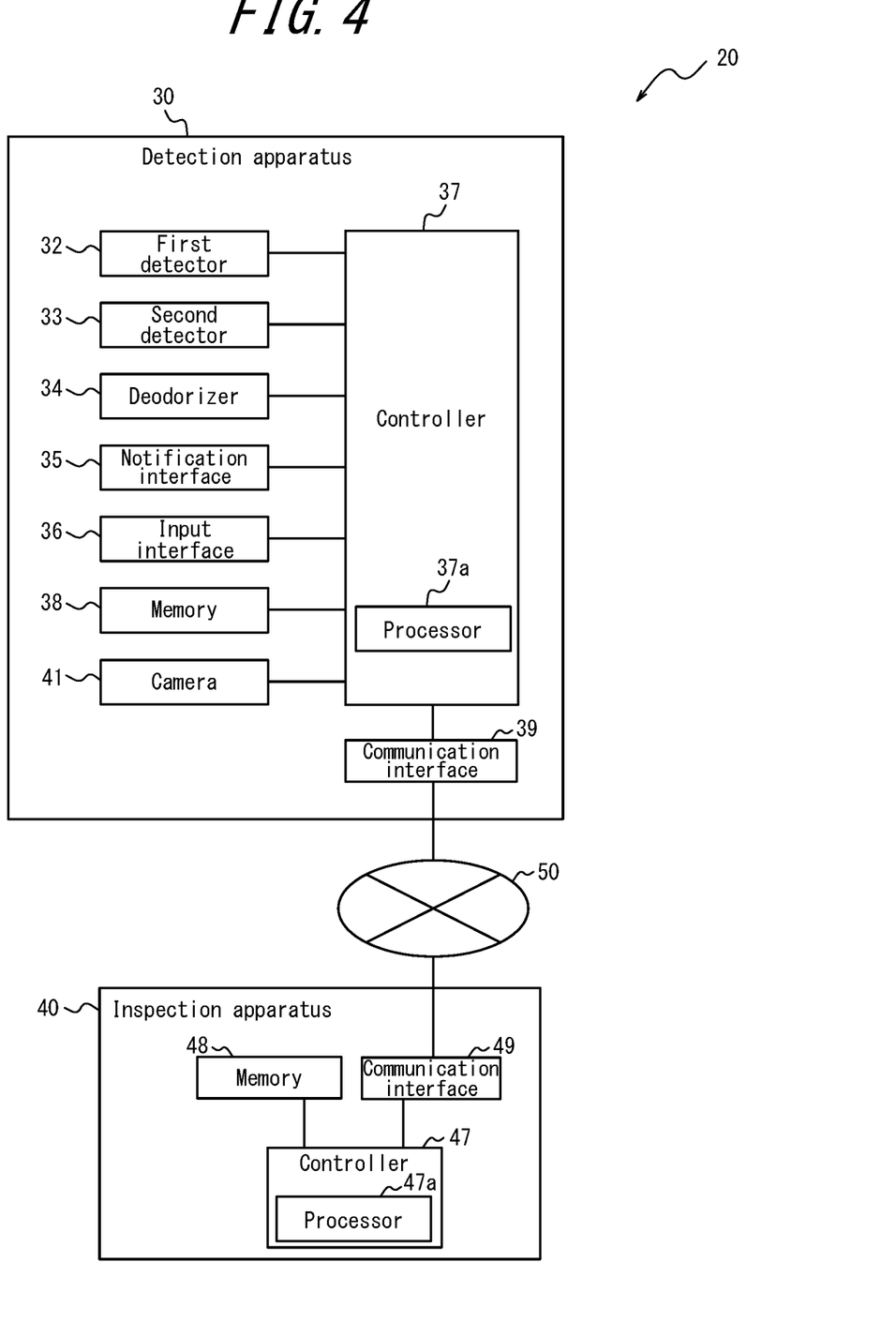
FIG. 4 is a functional block diagram illustrating the schematic configuration of an inspection system according to a second embodiment.

FIG. 4 is a functional block diagram illustrating the schematic configuration of an inspection system according to the second embodiment. As illustrated in FIG. 4, the inspection system 20 includes a detection apparatus 30 and an inspection apparatus 40. The detection apparatus 30 and the inspection apparatus 40 connect to allow communication therebetween over a network 50, such as an Internet connection, a wide area network (WAN), or a local area network (LAN).

The detection apparatus 30 may, for example, be configured as a container that includes a lid, as in the inspection apparatus 10 illustrated in FIG. 1. The detection apparatus 30 includes a first detector 32, a second detector 33, a deodorizer 34, a notification interface 35, an input interface 36, a controller 37, a memory 38, a communication interface 39, and a camera 41. The functions of the first detector 32, second detector 33, deodorizer 34, notification interface 35, input interface 36, and camera 41 are respectively similar to the functions of the first detector 12, second detector 13, deodorizer 14, notification interface 15, input interface 16, and camera 19 described with reference to FIG. 1. Hence, a description thereof is omitted.

The controller 37 controls and manages the detection apparatus 30 overall, starting with the functional blocks of the detection apparatus 30. To provide control and processing capability for executing various functions, the controller 37 may include at least one processor 37a. The controller 37 does not judge the quality of a food product, unlike the controller 17 described with reference to FIG. 2. The controller 37 transmits odor-related information acquired from the first detector 32 and moisture-related information acquired from the second detector 33 to the inspection apparatus 40 through the communication interface 39. The controller 37 may transmit information, related to the imaged specimen, acquired from the camera 41 to the inspection apparatus 40 through the communication interface 39.

From the inspection apparatus 40, the controller 37 acquires information related to the quality of a food product judged by the inspection apparatus 40. Upon acquiring the information related to the quality of the food product, the controller 37 provides notification of the information related to the quality of the food product through the notification interface 35. The controller 37 stores the information related to the quality of the food product in the memory 38.

The communication interface 39 exchanges a variety of information with the inspection apparatus 40 by wired or wireless communication. For example, the communication interface 39 transmits the odor-related information to the inspection apparatus 40. For example, the communication interface 39 receives the information related to the quality of the food product from the inspection apparatus 40. The odor-related information may, for example, be transmitted from the detection apparatus 30 to the inspection apparatus 40 each time the controller 37 acquires the odor-related information from the first detector 32. The odor-related information may, for example, be transmitted when the user provides predetermined operation input to the detection apparatus 30. The communication interface 39 may, for example, receive the information related to the imaged specimen from the detection apparatus 30.

The inspection apparatus 40 may, for example, be configured as a server. The inspection apparatus 40 includes a controller 47, a memory 48, and a communication interface 49.

The controller 47 controls and manages the inspection apparatus 40 overall, starting with the functional blocks of the inspection apparatus 40. To provide control and processing capability for executing various functions, the controller 47 may include at least one processor 47a. On the basis of the odor-related information and the moisture-related information that the communication interface 49 received from the detection apparatus 30, the controller 47 corrects the result of odor detection by the first detector 32 using the information related to the moisture, detected by the second detector 33, in the container. The controller 47 judges the quality of the food product on the basis of the corrected odor detection result. At this time, the controller 47 refers to information (data), stored in the memory 48, associating the odor emitted by a food product and the quality of the food product to judge the quality of the food product. The controller 47 transmits information related to the judged quality of the food product to the detection apparatus 30 through the communication interface 49. The controller 47 may judge the quality of the food product after inferring the type of food product on the basis of the information related to the imaged specimen.

By communicating with the detection apparatus 30 over the network 50, the communication interface 49 transmits and receives a variety of information. For example, the communication interface 49 receives the odor-related information and the moisture-related information from the detection apparatus 30. For example, the communication interface 49 transmits the information related to the quality of the food product to the detection apparatus 30.

In the inspection system 20 illustrated as an example in FIG. 4, the user can cause the detection apparatus 30 to detect odor-related information by using the detection apparatus 30 with a method similar to the method of using the inspection apparatus 10 described with reference to FIGS. 1 and 2. The user can learn the quality of the food product by the notification from the notification interface 35 of the detection apparatus 30.

In particular, since the inspection apparatus 40 that is a server judges the quality of the food product, the data in the memory 48 referred to by the controller 47 of the inspection apparatus 40 can be updated as necessary in the inspection system 20. In other words, the quality of the food product is judged on the basis of updated data in the inspection system 20.

In the second embodiment, both the process to correct the odor detection result and the process to judge the quality of the food product have been described as being executed by the controller 47 of the inspection apparatus 40, but either process, for example, may be executed by the controller 37 of the detection apparatus 30. For example, the controller 37 of the detection apparatus 30 may execute the process to correct the odor detection result, and the controller 47 of the inspection apparatus 40 may execute the process to judge the quality of the food product on the basis of the corrected information.

The present disclosure is not limited to the above embodiments, and a variety of modifications and changes are possible. For example, the functions and the like included in the components, steps, and the like may be reordered in any logically consistent way. Furthermore, components, steps, and the like may be combined into one or divided.

For example, the first detector 12 has been described in the above embodiment as being an odor sensor that detects an odor emitted by a food product, but the first detector 12 may be a sensor other than an odor sensor. For example, the first detector 12 may be a gas sensor that detects odorless gas molecules emitted by the specimen.

In the above embodiment, the second detector 13 has been described as being a humidity sensor, but the second detector 13 may be a sensor other than a humidity sensor, depending on the component to be detected. The second detector 13 may, for example, be a sensor that detects a different odor than the odor detected by the first detector 12. The second detector 13 may be a gas sensor that detects a different gas than the gas detected by the first detector 12. The second detector 13 may, for example, detect an odor or gas component that becomes noise during detection by the first detector 12. The gas detected by the second detector 13 may, for example, be alcohol, ester, ethylene, carbon dioxide, sulfur, ammonia, hydrogen, nitrogen, or the like.

In the above embodiment, the inspection apparatus 10 has been described as including the camera 19, but depending on the properties of the first detector 12 and the controller 17, for example, the inspection apparatus 10 need not include the camera.

The invention claimed is:

1. An inspection apparatus comprising:
a container configured to store a specimen;
a first detector configured to detect a substance emitted by the specimen stored in the container;
a second detector configured to detect a different component than the substance in an atmosphere inside the container;
a camera configured to capture an image of the specimen;
a memory configured to store a plurality of sets of information associating the substance and a quality of the specimen for each type of food products; and
a controller programmed to correct a result of detection of the substance by the first detector, on the basis of the component detected by the second detector, infer the type of food product of the specimen on the basis of information related to the image of the specimen captured by the camera, and judge the quality of the specimen based on the corrected result of detection of the substance and the inferred type of the food product of the specimen,
wherein the controller is programmed to refer to the information for the inferred type of the food product of the specimen stored in the memory, and judge the quality of the specimen stored in the container based on the corrected result of detection of the substance and the information corresponding to the inferred type of the food product of the specimen.

2. The inspection apparatus of claim 1, wherein the component is moisture.

3. The inspection apparatus of claim 1, wherein the inspection apparatus executes a refresh process of the container before the first detector detects the substance.

4. The inspection apparatus of claim 3, wherein the refresh process includes at least one selected from the group consisting of degassing the container, deodorizing the container, resetting the first detector, and resetting the second detector.

5. The inspection apparatus of claim 1, wherein the inspection apparatus executes a refresh process of the container after the first detector detects the substance.

6. The inspection apparatus of claim 1, further comprising a notification interface configured to provide notification of information related to the quality judged by the controller.

7. The inspection apparatus of claim 1, wherein
as the quality of the food product, the controller is configured to judge at least one selected from the group consisting of whether the food product is spoiled, whether the food product is ripe, a degree of aging of the food product, a freshness of the food product, a production area of the food product, and an extent of residual pesticide in the food product.

8. The inspection apparatus of claim 1, wherein the controller is programmed to execute a refresh process of the container, and the refresh process includes resetting the first detector and/or resetting the second detector.

9. The inspection apparatus of claim 1, wherein
as the quality of the food product, the controller is programed to judge a production area of the food product.

10. An inspection system comprising:
a detection apparatus; and
an inspection apparatus; wherein the detection apparatus comprises a container configured to store a specimen, a first detector configured to detect a substance emitted by the specimen stored in the container, a second detector configured to detect a different component than the substance in an atmosphere inside the container, a camera configured to capture an image of the specimen, and a communication interface configured to transmit information related to the substance detected by the first detector, information related to the component detected by the second detector to the inspection apparatus, and information related to the image of the specimen captured by the camera; and the inspection apparatus comprises a communication interface configured to receive the information related to the substance, the information related to the component, and the information related to the image of the specimen from the detection apparatus; a memory configured to store a plurality of sets of information associating the substance and a quality of the specimen for each type of food products; and a controller programmed to, on the basis of the received information related to the substance and the received information related to the component, correct a result of detection of the substance by the detection apparatus on the basis of the component, infer the type of food product of the specimen on the basis of the information related to the image of the specimen captured by the camera, and judge the quality of the specimen based on the corrected result of detection of the substance and the inferred type of the food product of the specimen, wherein the controller is programmed to refer to the information for the inferred type of the food product of the specimen stored in the memory, and judge the quality of the specimen based on the corrected result of detection of the substance and the information corresponding to the inferred type of the food product of the specimen.

11. The inspection apparatus of claim 8, wherein in the refresh process, the first detector and/or the second detector detectors are/is reset and an internal state of the container at the time of resetting is used as a reference to detect a change in the substance to be detected by the first detector and/or in the component to be detected by the second detector.

12. The inspection apparatus of claim 10, wherein the controller is programmed to execute a refresh process of the container, and the refresh process includes resetting the first detector and/or resetting the second detector.

13. The inspection apparatus of claim 12, wherein in the refresh process, the first detector and the second detector detectors are/is reset and an internal state of the container at the time of resetting is used as a reference to detect a change in the substance to be detected by the first detector and/or in the component to be detected by the second detector.

14. The inspection apparatus of claim 10, wherein
as the quality of the food product, the controller is programed to judge a production area of the food product.

* * * * *